United States Patent [19]

Reissenweber

[11] 4,316,020

[45] Feb. 16, 1982

[54] PREPARATION OF ISATOIC ANHYDRIDES

[75] Inventor: Gernot Reissenweber, Ludwigshafen, Fed. Rep. of Germany

[73] Assignee: BASF Aktiengesellschaft, Fed. Rep. of Germany

[21] Appl. No.: 155,761

[22] Filed: Jun. 2, 1980

[30] Foreign Application Priority Data

Jun. 22, 1979 [DE] Fed. Rep. of Germany ....... 2925175

[51] Int. Cl.³ .......................................... C07D 265/26
[52] U.S. Cl. .................................................. 544/105
[58] Field of Search ........................................ 544/105

[56] References Cited

U.S. PATENT DOCUMENTS 3,238,201 3/1966 Scherrer ............................ 544/105

OTHER PUBLICATIONS

Erdmann et al., Ber. Deut. Chem., vol. 32, pp. 2159 to 2172 (1899).
Kolbe, J. Prakt. Chem., vol. 30, pp. 84–87, 467 to 483 (1884).
Mohr, J. Prakt. Chem., vol. 80, pp. 1–24 (1909).
The Merck Index, 9th Ed., Conant, The Chemistry of Organic Compounds, pp. 402–403, the Macmillan Company, NY Sixth Printing 1943.
Krow, Synthesis, pp. 50 to 51, Jan. 1979 (copyrighted 1979 Georg Thieme Publishers).

*Primary Examiner*—John D. Randolph
*Attorney, Agent, or Firm*—Keil & Witherspoon

[57] ABSTRACT

A process for the preparation of isatoic anhydrides of the formula

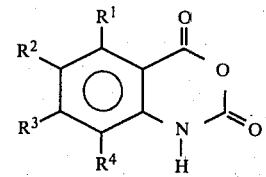

where $R^1$, $R^2$, $R^3$ and $R^4$ are identical or different and each is hydrogen, alkyl, alkoxy, halogen, nitro, haloalkyl or haloalkoxy, by reacting an isatin of the formula

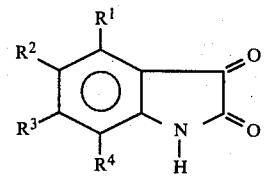

where $R^1$, $R^2$, $R^3$ and $R^4$ have the stated meanings, with hydrogen peroxide in an acid medium.

2 Claims, No Drawings

PREPARATION OF ISATOIC ANHYDRIDES

The present invention relates to a novel process for the preparation of isatoic anhydrides.

Isatoic anhydrides may be prepared, for example, by reacting an anthranilic acid with ethyl chloroformate or with phosgene (Chem. Ber. 32 (1898), 2163–2164). The substituted anthranilic acids required as starting materials are however difficult to prepare, for example by alkaline oxidation of isatin derivatives:

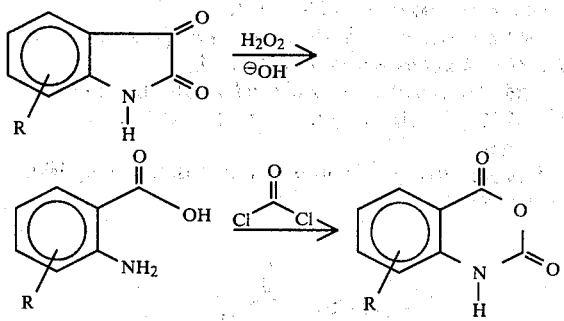

Another method of obtaining isatoic anhydrides is to oxidize substituted phthalimides (J. prakt. Chemie [2] 80 (1909), 1–24). This, however, as a rule gives isomer mixtures:

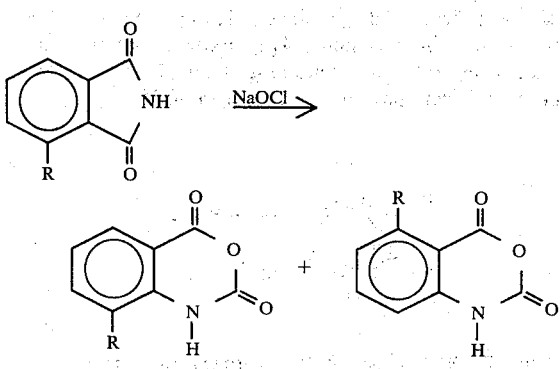

It is also known that N-phenyl-substituted isatins may be converted to the corresponding isatoic anhydride by a very expensive method employing peracids (U.S. Pat. No. 3,238,201). Hitherto, chromium trioxide in glacial acetic acid or acetic anhdyride was regarded as the only suitable oxidizing agent for N-unsubstituted isatins (J. prakt. Chem. 30 (1884), 84 and 467). However, mixtures of chromium trioxide and glacial acetic acid or acetic anhydride are prone to explode. Furthermore, the fact that chromium is toxic presents additional safety problems.

I have found a novel process for the preparation of isatoic anhydrides of the formula I

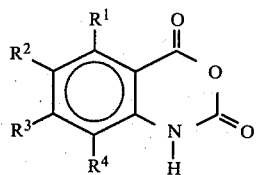

where $R^1$, $R^2$, $R^3$ and $R^4$ are identical or different and each is hydrogen, alkyl, alkoxy, halogen, nitro, haloalkyl or haloalkoxy, wherein an isatin of the formula II

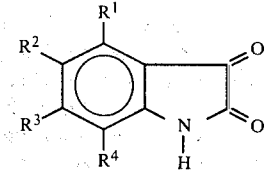

where $R^1$, $R^2$, $R^3$ and $R^4$ have the above meanings, is reacted with hydrogen peroxide in an acid medium.

For the purposes of the invention, alkyl, alkoxy, haloalkyl and haloalkoxy radicals are preferably of 1 to 4 carbon atoms.

To carry out the process according to the invention, an isatin of the formula II is dissolved or suspended in a carboxylic acid and an aqueous hydrogen peroxide solution is added dropwise. Suitable solvents are aliphatic carboxylic acids and halogen-substituted aliphatic carboxylic acids, especially formic acid, acetic acid, propionic acid, chloroacetic acid, trifluoroacetic acid and mixtures of these acids. The hydrogen peroxide solution may be of any commercial concentration but is preferably a 30 percent strength or 50 percent strength aqueous solution. The hydrogen peroxide is employed in the molar ratio of 1:1, based on isatin, or, preferably, in a slight excess, up to a molar ratio of 2:1. The reaction may be carried out at from 0° to 100° C., but is most advantageously carried out at room temperature, or slightly above this (25°–65° C.). The addition of an inorganic acid or aromatic carboxylic acid accelerates the reaction. Examples of preferred acids are sulfuric acid, phosphoric acid and p-toluenesulfonic acid. From 1 to 50 parts, particularly advantageously from 1 to 5 parts, of acid may be added per 100 parts of solvent.

The desired isatoic anhydrides are obtained in a crystalline form during the reaction and can thus be isolated easily by conventional methods, for example by filtering or centrifuging.

Compared to the conventional methods, the novel process starts from easily available materials and gives the desired compounds in a surprisingly simple and very economical manner, in high yield and high purity.

Isatoic anhydrides are valuable intermediates for the preparation of drugs and crop protection agents. For example, reaction of an isatoic anhydride with isopropylamine gives the corresponding anthranilic acid isopropylamide, from which 2,1,3-thiadiazin-4-one-2,2-dioxide derivatives, which are known crop protection agents, may be prepared (German Laid-Open Application DOS No. 2,710,382).

EXAMPLE 1

16.1 parts of 7-methylisatin are suspended in 150 parts of glacial acetic acid and 2.5 parts of concentrated sulfuric acid. 15 parts of 30 percent strength hydrogen peroxide solution are added dropwise at 35° C. over 10 minutes, and the suspension is then stirred for two hours at 60° C. When it has cooled, the precipitate is filtered off and washed with water. 14.2 parts of 8-methylisatoic anhydride are obtained; melting point 236°–238° C., with decomposition.

The same result is obtained if the acetic acid is replaced by a 2:1 mixture of acetic acid and chloroacetic acid or of acetic acid and trifluoroacetic acid.

EXAMPLE 2

14.7 parts of isatin are suspended in 80 parts of formic acid. 20 parts of 30 percent strength hydrogen peroxide solution are added dropwise, with slight cooling. The mixture is then stirred for 60 minutes at 25° C., after which it is worked up in a conventional manner. 13.2 parts of isatoic anhydride are obtained; melting point 252°–253° C., with decomposition.

EXAMPLE 3

41 parts of 6-fluoroisatin are suspended in 500 parts of glacial acetic acid and 15 parts of concentrated sulfuric acid and 100 parts of 30 percent strength hydrogen peroxide solution are added at 30° C. A slightly exothermic reaction is observed and at 40°–45° C. a clear solution is temporarily produced. The temperature is not allowed to rise above 50° C., and after one hour the mixture is cooled to room temperature. The precipitate is filtered off and washed. 38 parts of 7-fluoroisatoic anhydride are obtained; melting point 229°–231° C., with decomposition.

EXAMPLE 4

108 parts of 5,7-dichloroisatin are added to a solution, pre-heated to 40° C., of 900 parts of glacial acetic acid and 15 parts of sulfuric acid, and 80 parts of 50 percent strength hydrogen peroxide solution are then added slowly. The temperature is allowed to rise to 65° C. The suspension dissolves and after a few minutes the desired product begins to precipitate from the warm solution. Stirring is continued for one hour and after cooling 103 parts of 6,8-dichloroisatoic anhydride are obtained; melting point 254°–256° C., with decomposition.

EXAMPLE 5

16.1 parts of 7-methylisatin are suspended in a mixture of 120 parts of glacial acetic acid and 10 parts of formic acid and 15 parts of 30 percent strength hydrogen peroxide solution are added at 50° C. The mixture is stirred for 2.5 hours at 50° C., and after cooling 12.6 parts of 8-methylisatoic anhydride are obtained; melting point 237°–239° C., with decomposition.

EXAMPLE 6

43 parts of 7-trifluoromethylisatin are suspended in 130 parts of glacial acetic acid and 2.5 parts of sulfuric acid and 25 parts of 30 percent strength hydrogen peroxide solution are added at 40° C. After stirring the mixture for one hour at not above 55° C., 38 parts of 8-trifluoromethylisatoic anhydride are obtained; melting point 184°–186° C., with decomposition.

The following were prepared by a similar method:
6-Bromo-8-methylisatoic anhydride, melting point >270° C., in 80% yield.
6-Fluoroisatoic anhydride, melting point 265°–268° C., with decomposition, in 83% yield.
6-Bromoisatoic anhydride, melting point 270°–275° C., with decomposition, in 83% yield.
6-Nitroisatoic anhydride, melting point 224°–232° C., with decomposition, in 80% yield.
8-Chloroisatoic anhydride, melting point 210°–215° C., with decomposition, in 85% yield.
5-Methyl-8-methoxyisatoic anhydride, melting point 235°–242° C., with decomposition, in 75% yield.

I claim:

1. A process for the preparation of isatoic anhydrides of the formula I

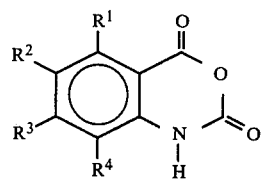

where $R^1$, $R^2$, $R^3$ and $R^4$ are identical or different and each is hydrogen, alkyl, alkoxy, halogen, nitro, haloalkyl or haloalkoxy, said alkyl, alkoxy, haloalkyl and haloalkoxy radicals containing from 1 to 4 carbon atoms, wherein an isatin of the formula II

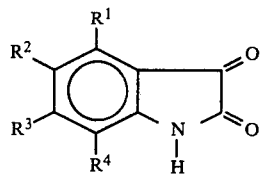

where $R^1$, $R^2$, $R^3$ and $R^4$ have the above meanings, is reacted with hydrogen peroxide in an acid medium.

2. The process of claim 1, wherein the reaction is carried out in the presence of from 1 to 50, preferably from 1 to 5, parts of an inorganic acid per 100 parts of solvent.

* * * * *